United States Patent [19]
Smyth

[11] Patent Number: 6,053,086
[45] Date of Patent: Apr. 25, 2000

[54] ROTARY SUTURE CUTTING APPARATUS AND METHOD OF USE

[75] Inventor: Charles J. Smyth, Orange, Conn.

[73] Assignee: United States Surgical Corporation, Norwalk, Conn.

[21] Appl. No.: 08/869,847

[22] Filed: Jun. 5, 1997

Related U.S. Application Data

[62] Division of application No. 08/598,296, Feb. 8, 1996, Pat. No. 5,639,506.

[51] Int. Cl.$^7$ ...................................................... B26D 7/00
[52] U.S. Cl. ................................ 83/648; 83/821; 83/658; 83/663; 83/949; 83/950
[58] Field of Search ............................ 83/175, 658, 648, 83/649, 821, 663, 673, 675, 676, 949, 909, 950, 542; 427/177, 175, 290, 293, 358, 231

[56] References Cited

U.S. PATENT DOCUMENTS

| | | |
|---|---|---|
| D. 353,672 | 12/1994 | Swor . |
| 3,447,409 | 6/1969 | Lewis ......................................... 83/614 |
| 3,561,312 | 2/1971 | Jones ......................................... 83/614 |
| 3,624,683 | 11/1971 | Matles . |
| 3,659,343 | 5/1972 | Straus . |
| 3,686,991 | 8/1972 | Fujimoto ................................... 83/614 |
| 3,821,915 | 7/1974 | Larrable ..................................... 83/649 |
| 3,879,846 | 4/1975 | Allen, Jr. . |
| 3,990,144 | 11/1976 | Schwartz . |
| 4,034,473 | 7/1977 | May . |
| 4,053,979 | 10/1977 | Tuthill et al. . |
| 4,141,115 | 2/1979 | Fourne et al. . |
| 4,204,443 | 5/1980 | McLuskie . |
| 4,271,838 | 6/1981 | Lasner et al. . |
| 4,369,787 | 1/1983 | Lasner et al. . |
| 4,384,406 | 5/1983 | Tischlinger . |
| 4,406,196 | 9/1983 | Roncato et al. . |
| 4,461,060 | 7/1984 | Mannhart . |
| 4,494,542 | 1/1985 | Lee . |
| 4,662,068 | 5/1987 | Polonsky . |
| 4,845,851 | 7/1989 | Warthen . |
| 4,848,341 | 7/1989 | Ahmad . |
| 4,949,717 | 8/1990 | Shaw . |
| 4,969,893 | 11/1990 | Swor . |
| 4,984,941 | 1/1991 | White et al. . |
| 5,007,922 | 4/1991 | Chen et al. . |
| 5,015,252 | 5/1991 | Jones . |
| 5,016,353 | 5/1991 | Iten . |
| 5,044,241 | 9/1991 | Labrecque ................................. 83/649 |
| 5,080,667 | 1/1992 | Chen et al. . |
| 5,084,058 | 1/1992 | Li . |
| 5,133,723 | 7/1992 | Li et al. . |
| 5,163,946 | 11/1992 | Li . |
| 5,196,023 | 3/1993 | Martin . |
| 5,226,336 | 7/1993 | Coates . |
| 5,243,890 | 9/1993 | Ober ......................................... 83/614 |
| 5,250,247 | 10/1993 | Chesterfield et al. . |
| 5,269,808 | 12/1993 | Proto et al. . |
| 5,322,001 | 6/1994 | Boda ......................................... 83/455 |
| 5,331,877 | 7/1994 | Ishii .......................................... 83/676 |
| 5,346,500 | 9/1994 | Suchart . |
| 5,374,278 | 12/1994 | Chesterfield et al. . |
| 5,383,877 | 1/1995 | Clarke . |
| 5,385,569 | 1/1995 | Swor . |
| 5,398,576 | 3/1995 | Chiu ......................................... 83/649 |
| 5,417,702 | 5/1995 | Hempel . |
| 5,431,077 | 7/1995 | Murakami ................................ 83/614 |
| 5,437,726 | 8/1995 | Proto et al. . |
| 5,440,961 | 8/1995 | Lucas, Jr. et al. ........................ 83/614 |
| 5,452,513 | 9/1995 | Zinnbauer et al. . |
| 5,452,636 | 9/1995 | Ruttan . |
| 5,671,647 | 9/1997 | Mori ......................................... 83/614 |
| 5,779,851 | 7/1998 | Ifkovits et al. ........................... 83/676 |

*Primary Examiner*—M. Rachuba

[57] ABSTRACT

A rotary suture cutting apparatus includes a base having an upper resilient layer, and a cutting assembly. The cutting assembly includes a frame and a rotary cutting tool having a disk shaped circular blade. The cutting tool is slidably mounted to the frame and when moved from one end to the other of the frame, cleanly slices suture material clamped between the base and the cutting assembly without brooming, fraying or otherwise disporting the cut suture tip. A method of preparing cut suture lengths is also provided

12 Claims, 4 Drawing Sheets ism 150 comprising an elongated latch 151 attached to the cutting frame 111 and a stop member or catch 152 attached

ROTARY SUTURE CUTTING APPARATUS AND METHOD OF USE

This is a divisional of U.S. application Ser. No. 08/598,296 filed Feb. 8, 1996 now U.S. Pat. No. 5,639,506.

BACKGROUND

1. Technical Field

The disclosure herein relates to preparing cut lengths of surgical sutures, and more particularly to a device for cutting a suture to a desired length with minimum end distortion for attachment to a needle.

2. Background of the Art

Surgical sutures are known in the art and can be multifilament or monofilament as well as bioabsorbable or non-bioabsorbable. Typically, sutures are attached to surgical needles as needle-suture combinations. The surgical needles generally have an aperture into which the end of a suture is inserted and secured by, for example, crimping or swaging the needle. Prior to insertion, the suture end is prepared by cutting.

Multifilament sutures have a tendency to "broom," i.e., the filaments tend to spread out at the end after the cut is made. Because the needle aperture size and suture diameter are dimensionally close, distortion of the suture end, such as that caused by brooming, makes it difficult to insert the suture end into the needle aperture. Hence, multifilament sutures are preferably tipped prior to cutting with an appropriate tipping agent which causes the filaments to adhere to each other. Tipping the suture facilitates the insertion of the suture end into the needle aperture by preventing brooming of the cut filaments.

Cutting is usually performed by passing a sharp edged cutting blade (e.g., razor blade or scissors) laterally across the suture at the tipped portion. However, this manner of cutting can cause abrasion of the suture because pressure is applied laterally, and distortion of the suture end can arise from the cutting process even when the end has been tipped Accordingly, what is needed is a method and apparatus for cutting a suture which minimizes distortion.

SUMMARY

A rotary suture cutting apparatus is provided herein. The apparatus includes a base having an upper resilient layer, and a cutting assembly. The cutting assembly includes a frame, and a rotary cutting tool having a disk shaped circular blade, the rotary cutting tool being slidably mounted to the frame. The cutting assembly is removably attachable to the base. In a preferred embodiment, the apparatus is adapted for use with a suture winding drum in connection with a tipping process wherein a suture is wound around the drum with a portion being tipped with a tipping agent. The base of the cutting apparatus is inserted into a slot in the drum and held together with the cutting assembly, such as by clamping the base and cutting apparatus together, with the suture held between them. The rotary cutting tool is then moved longitudinally along the frame, and rotates by frictional engagement with the base layer and suture to cleanly cut the suture as the blade rolls over it The resilient layer of the base is optimally a self healing polymeric material preferably polyvinyl chloride sheet.

BRIEF DESCRIPTION OF THE DRAWINGS

Various embodiments are described herein with reference to the drawings above.

DETAIL DESCRIPTION OF A PREFERRED EMBODIMENT

Figure 1:
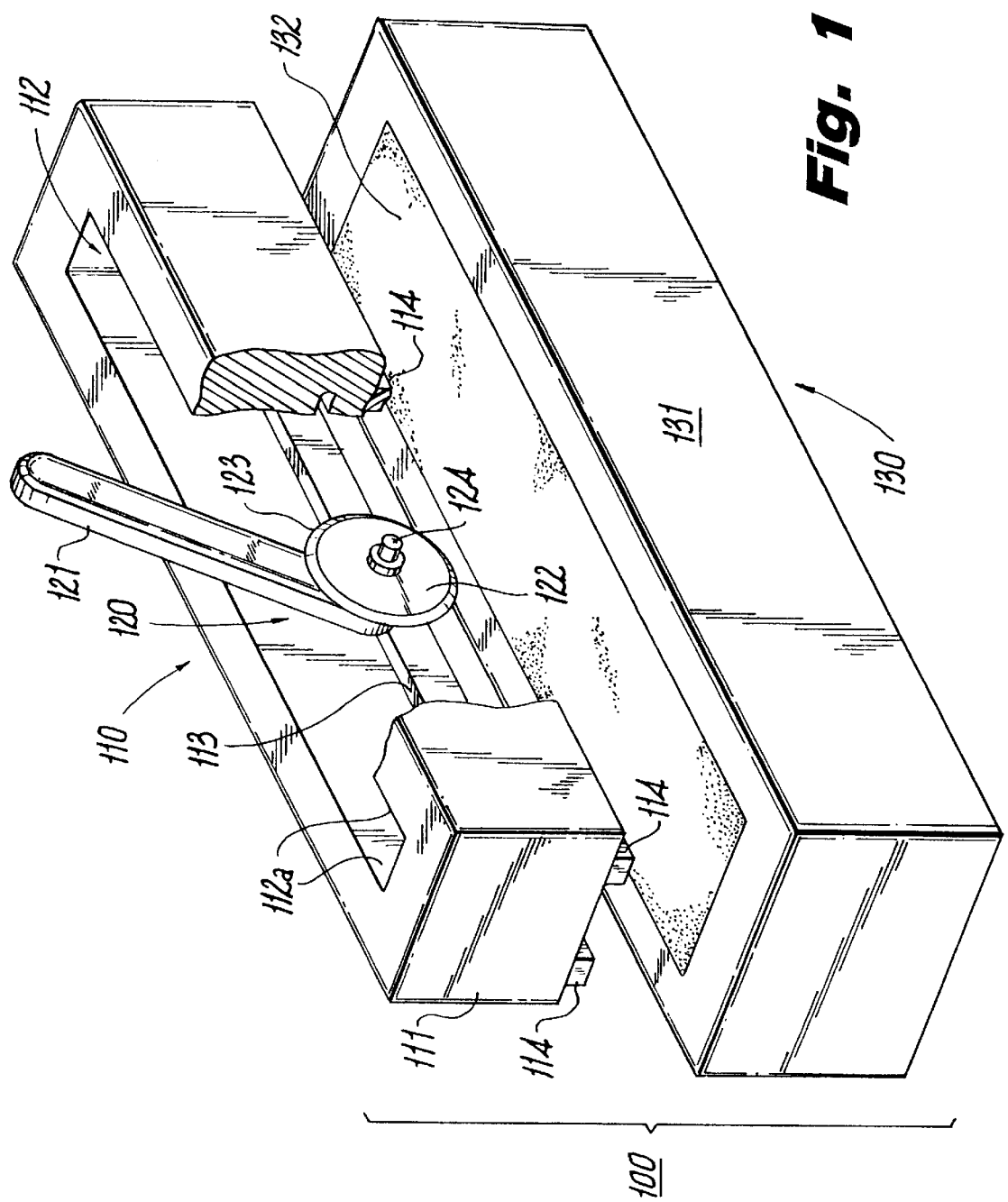
FIG. 1 is a partially cut away perspective view of the rotary suture cutting apparatus.

Referring to FIG. 1, the apparatus 100 comprises an upper cutting assembly 110, and a lower base block 130. The cutting assembly 110 and base block 130 are adapted to be used in conjunction with each other for cutting laterally orientated sutures positioned therebetween.

The upper cutting assembly 110 includes a cutting frame 111 which is preferably a substantially rectangular block having a lengthwise slot 112 and two lengthwise extending notches 113 on the parallel interior side walls 112a of the slot 112. Notches 113 serve as block axle tracks, as discussed below. Cutting assembly 110 also includes two rubber feet 114 extending lengthwise along the bottom of the cutting frame 111. The rubber feet grip the suture adjacent the portion to be cut without damaging the suture. The upper cutting assembly 100 also includes a rotary cutting tool 120 which is positioned within slot 112 and adapted to be moved lengthwise along the slot 112. The lengthwise slot 112 is open at the top and bottom of the frame 112 and functions as a guide for rotary cutting tool 120.

Cutting frame 111 is preferably fabricated from a rigid material of sufficient strength for the purposes described herein. Such material can be a metal (for example, stainless steel) or a hard plastic (for example, polycarbonate, or polymethyl methacrylate). The rubber feet 114 should be fabricated from a soft rubbery material, preferably a silicone rubber, which is sufficiently soft to avoid abrasion or other damage to the suture.

The rotary cutting tool 120 includes an elongated handle 121, and a circular blade 122 rotatably mounted to an axle 124 attached to the handle 121. Circular blade 122 has a razor edge 123. A cutting tool suitable for use in the present invention is commercially available as model RTY-3/G rotary cutter from Olfa Corporation of Osaka, Japan.

Figure 5:
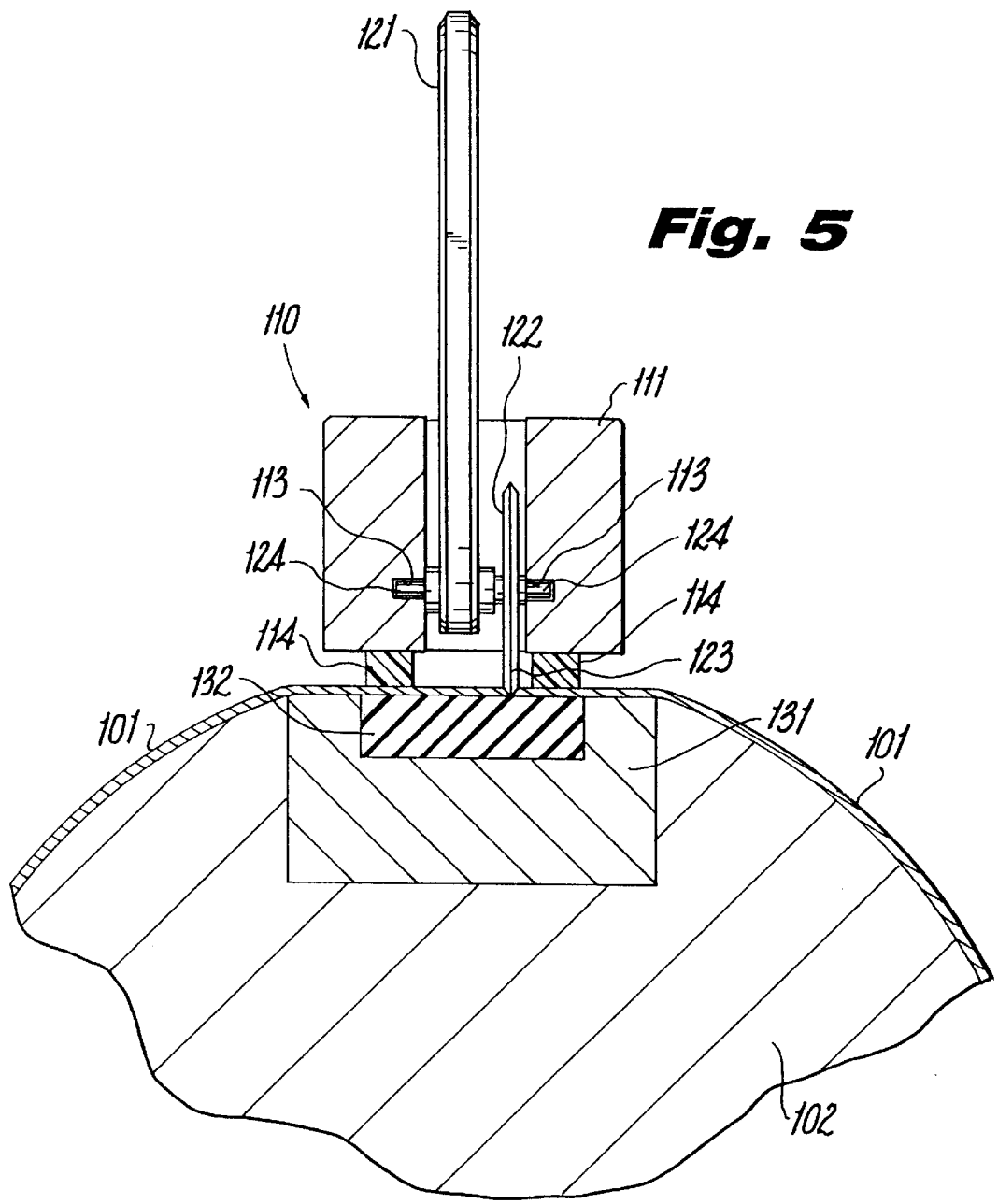
FIG. 5 is a sectional end view of the rotary suture cutting apparatus in conjunction with a suture winding drum and suture material positioned therebetween.

Referring to FIGS. 1 and 5, the axle 124 of the rotary cutter is preferably of such length as to extend laterally outward on both sides of the cutting tool 120 so as to be received into guide notch 113 on both side walls 112a of aperture 112. The circular blade 122 is dimensioned so as to extend below feet 114 a sufficient distance such that cutting edge 123 meets the top surface of cutting layer 132 to cut a suture placed on base block 130.

Figure 4:
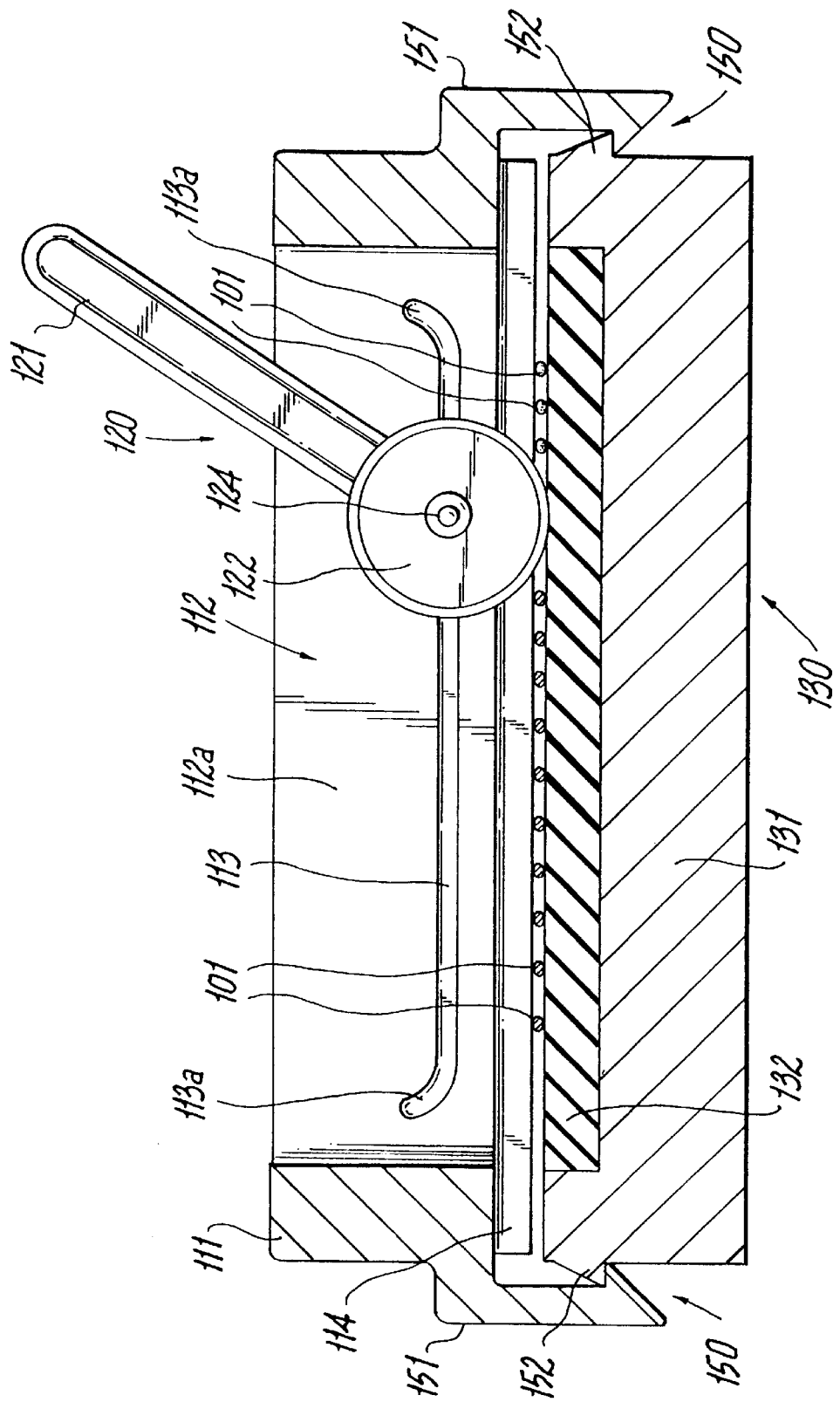
FIG. 4 is a sectional elevational side elevational view of the cutting assembly clamped to the base block with suture material therebetween.

Referring additionally to FIG. 4, notch 113 preferably has upwardly curved end portions 113a which serve to lift the rotary cutting tool 120 a sufficient distance such that blade edge 123 does not extend below the feet 114 and is out of contact with the base block 130 and/or suture.

The apparatus can optionally include a clamping mechanism 150 comprising an elongated latch 151 attached to the cutting frame 111 and a stop member or catch 152 attached to the base block 130. Elongated latch 151 bends resiliently to engage catch 152 when the cutting frame 111 and the base block 130 are assembled. Latch 151 is manually disengaged from catch 152 by bending it outward. It will be appreciated that many alternative types of clamping mechanisms known to those with skill in the art, such as clamps involving springs, air, cams, bolts, etc., can be employed Referring to FIGS. 1, 4 and 5, the base block 130 comprises a rectangular body portion 131 having an upper layer 132 of soft polymeric material. Preferably, layer 132 is a sheet of self-healing polyvinyl chloride ("PVC") resin. A material suitable for use as layer 132 is available as X-ACTO® model X7761 self healing mat, or the OLFA® rotary mat model RM-CG available from the Olfa Corporation.

Figure 2:
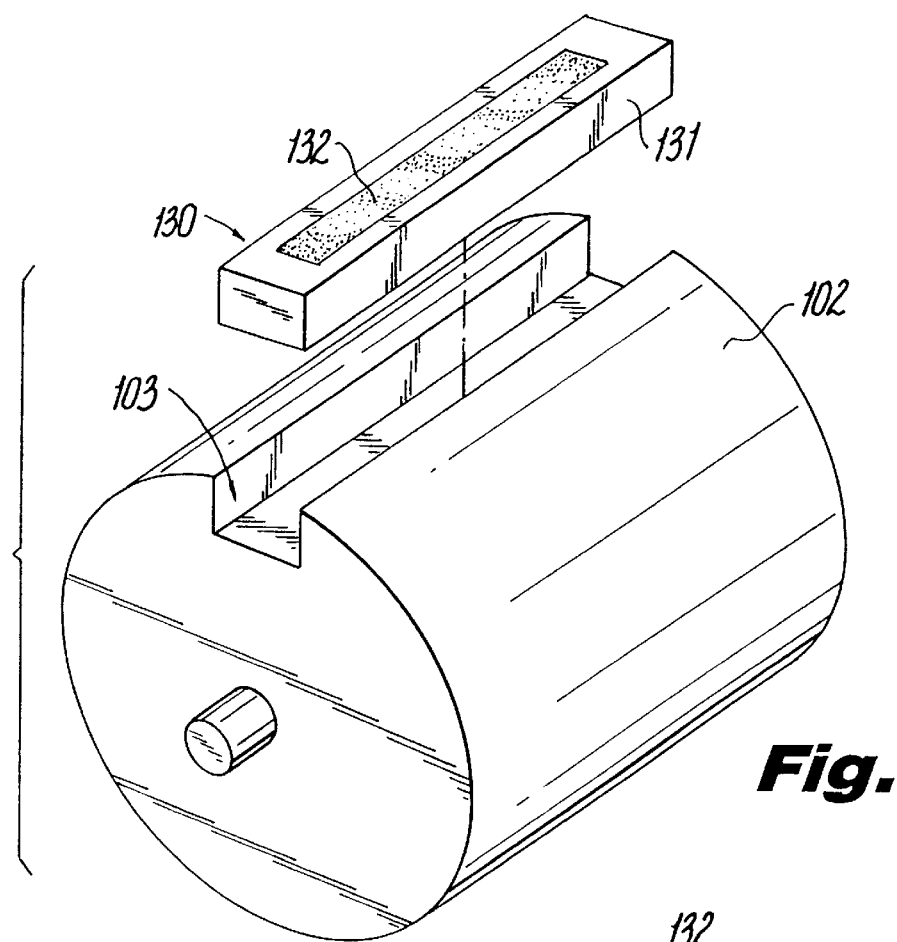
FIG. 2 is an exploded perspective view of the base block and a suture winding drum.
Figure 3:
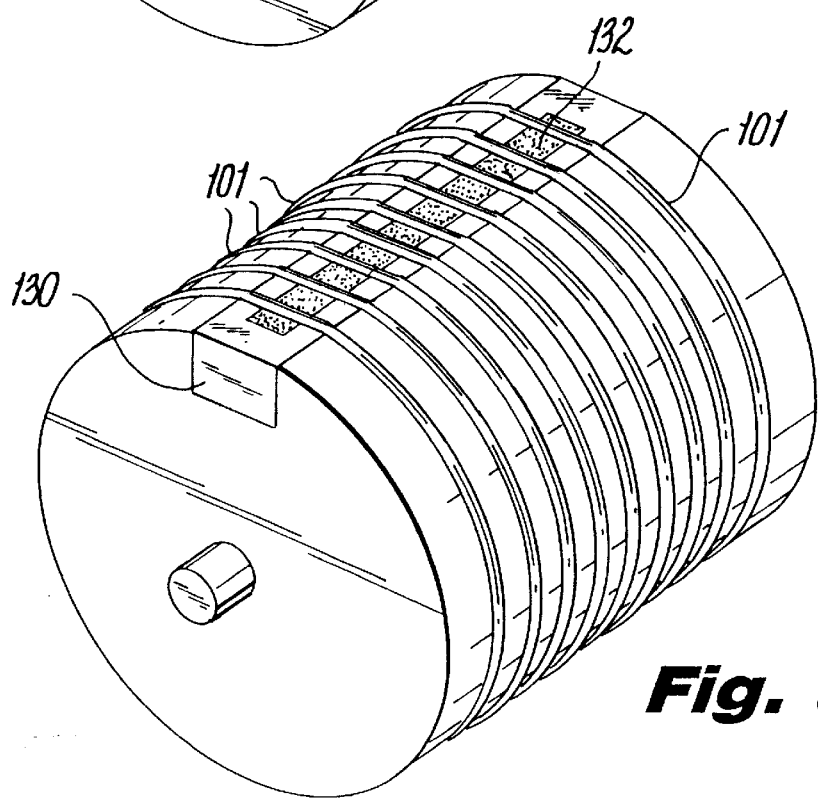
FIG. 3 is a perspective view showing the base block inserted into a suture winding drum with a suture wound therearound.

Referring to FIGS. 2 and 3, the base block 130 is configured and dimensioned to be received into slot 103 in a suture winding drum 102. The suture winding drum 102 is used in tipping operations wherein a length of suture material is wound around drum 102, and tipping agent is applied to the portion of the suture extending across notch 103, for example, by spraying. An apparatus and procedure for tipping sutures with a cyanoacrylate tipping agent using a drum is disclosed and described in U.S. Pat. No. 5,269,808 to Proto et al., herein incorporated by reference.

One procedure for tipping and cutting sutures is to wind the suture material 101 around the drum 102, apply tipping agent (e.g., a mist of monomeric cyanoacrylate) to the suture portions extending across open slot 103, then insert the base block 130 into slot 103 from the side after the tipping agent has been permitted to cure. Next the cutting assembly 110 is clamped to the base block 130 and the rotary cutting tool is passed lengthwise along cutting frame 111 to cut the suture 101.

An advantageous feature of this method and apparatus is that the rotary blade 122 does not apply pressure laterally to the suture 101, that is, a blade is not dragged across the suture. Instead, blade edge 123 rolls over the suture and slices it cleanly by pressing down on it. The suture 101 is supported by the self healing layer 132 in the vicinity of the cut. The rubbery feet 114 and the self healing layer 132 have sufficient softness and resiliency to prevent damage to the suture when the cutting assembly 110 and base block 130 are clamped together.

It will be understood that various modifications may be made to the embodiments described herein. Therefore, the description should not be construed as limiting, but merely as exemplifications of preferred embodiments. For example, while the apparatus described herein is advantageous for cutting multifilament sutures in conjunction with a tipping process, it can be used for cutting, non-tipped monofilament sutures, for example, from an annealing rack or drum. Those skilled in the art will envision other modifications within the scope and spirit of the claims appended hereto.

What is claimed is:

1. An apparatus for cutting a suture comprising:
    a) a base having an upper resilient layer; and
    b) a cutting assembly including a frame, and a rotary cutting tool having a disk shaped circular blade, the rotary cutting tool being slidably mounted to the frame, and said cutting assembly being removably attachable to the base, wherein the frame is elongated and includes an elongated aperture at least partially defined by two lengthwise extending interior side walls, each of the lengthwise extending side walls including a lengthwise extending notch having at least one upwardly curved notch end portion, the circular blade being rotatably mounted on an axle having first and second axle end portions, each axle end portion being slidably received into a respective one of the lengthwise extending notches of the side wall.

2. The apparatus of claim 1 wherein the upper resilient layer of the base is fabricated from a self healing polymeric material.

3. The apparatus of claim 1 wherein the rotary cutting tool comprises an elongated handle, the axle extending laterally through the handle.

4. The apparatus of claim 1 wherein the cutting assembly includes elongated resilient feet.

5. The apparatus of claim 1 wherein the frame is constructed from a rigid material.

6. The apparatus of claim 1 further comprising a suture winding drum having a slot into which the base is received.

7. The apparatus of claim 1 further including a clamp for releasably joining the base and the cutting assembly.

8. In combination:
    a substantially cylindrical drum for winding suture material, the drum having a longitudinal notch therein;
    a base having an upper resilient layer, the base receivable within the notch;
    a cutting assembly including a frame, and a rotary cutting tool having a disk shaped cutting blade with a cutting edge at the periphery thereof, the cutting assembly being releasably mountable to the base and the cutting blade being longitudinally movable along the frame with the cutting edge in contact with the resilient layer, wherein the frame is elongated and includes an elongated aperture at least partially defined by two lengthwise extending side walls, each of the lengthwise extending side walls including a lengthwise extending notch with at least one upwardly curved notch end portion, the circular blade being rotatably mounted on an axle having first and second axle end portions, each axle end portion being slidably received into a respective one of the lengthwise extending notches of the wall.

9. The combination of claim 8 further comprising a length of suture material wound around the drum.

10. The combination of claim 9, wherein the suture material is a monofilament suture material.

11. The combination of claim 9 wherein the suture material is a multifilament suture material.

12. The combination of claim 11 wherein a portion of the suture material extending across the notch is tipped with a tipping agent.

* * * * *